US007013588B2

(12) United States Patent
Chang

(10) Patent No.: US 7,013,588 B2
(45) Date of Patent: Mar. 21, 2006

(54) FLOATING MASSAGE PAD STRUCTURE

(76) Inventor: Freddie Chang, 995 Singing Wood Ave., Arcadia, CA (US) 91006

( * ) Notice: Subject to any disclaimer, the term of this patent is extended or adjusted under 35 U.S.C. 154(b) by 0 days.

(21) Appl. No.: 10/846,452

(22) Filed: May 14, 2004

(65) Prior Publication Data

US 2004/0230139 A1 Nov. 18, 2004

(30) Foreign Application Priority Data

Apr. 15, 2003 (TW) ................................. 92208910

(51) Int. Cl.
*A61F 5/14* (2006.01)

(52) U.S. Cl. ........................................................ 36/141

(58) Field of Classification Search .................. 36/141; 600/9; 601/15

See application file for complete search history.

(56) References Cited

U.S. PATENT DOCUMENTS 3,625,204 A 12/1971 Sekiguchi
4,033,054 A * 7/1977 Fukuoka ...................... 36/11.5
4,047,310 A 9/1977 Sunoo
4,067,125 A * 1/1978 Greene, Sr. ................. 36/35 R
4,095,353 A 6/1978 Foldes
4,509,510 A 4/1985 Hook
4,598,484 A * 7/1986 Ma ............................. 36/3 R
4,727,661 A 3/1988 Kuhn
4,843,738 A * 7/1989 Masuda ......................... 36/44
5,096,188 A 3/1992 Shen
5,186,703 A 2/1993 Huang
5,405,310 A 4/1995 Yoo
5,502,901 A * 4/1996 Brown .......................... 36/28
5,551,173 A 9/1996 Chambers
5,553,398 A * 9/1996 Schnewlin-Maier ........... 36/43
5,607,749 A 3/1997 Strumor
5,682,690 A * 11/1997 Chang ......................... 36/141
5,685,094 A * 11/1997 Lin ............................ 36/141
5,860,229 A 1/1999 Morgenstern
6,082,024 A 7/2000 Del Biondi
6,241,695 B1 6/2001 Dabir
6,434,859 B1 8/2002 Kim
6,715,221 B1 * 4/2004 Sasaki ......................... 36/141
2004/0230139 A1 * 11/2004 Chang ......................... 601/15

* cited by examiner

*Primary Examiner*—Ted Kavanaugh
(74) *Attorney, Agent, or Firm*—Jeffer, Mangels, Butler & Marmaro LLP

(57) ABSTRACT

The present invention discloses a floating massage pad structure having several messaging protrusions which normally float under to facilitate the rubbing and message made by the massage pad structure, comprising a flexible pad, a plurality of floating chambers in some portions within the surface that provide a plurality of mushroom-shaped massage protrusions; an opposing member disposed below the massage protrusion; a pair of repulsive magnetic members respectively disposed on the massage protrusion and the corresponding opposing member, such that the repulsion of the magnetic members makes the massage protrusions float under normal conditions, giving a sense of touching our skin before the massage, providing a multi-directional massage during the massage, and having a caressing effect after the massage.

9 Claims, 8 Drawing Sheets

FLOATING MASSAGE PAD STRUCTURE

RELATED PATENT APPLICATION INFORMATION

This application claims foreign priority benefits under 35 U.S.C. 119(a)–(d) from Taiwan patent application Ser. No. 92208910, filed on May 15, 2003 in the Taiwanese Intellectual Property Office.

FIELD OF THE INVENTION

The present invention relates to a floating massage pad structure, more particularly a massage pad having a plurality of massage protrusions which float under normal conditions to give the sense of touching the acupunctural points before the massage process, and to provide a multi-directional massage during the massage process as well as a caressing effect afterward. This invention can also be applied to shoes, providing looser fastening to the shoes for more comfortable wear.

BACKGROUND OF THE INVENTION

Please refer to FIG. 1 for the prior-art design disclosed in R.O.C. Patent Publication No. 265537, comprising a cylindrical body 20 disposed at the bottom of a sole, the cylindrical body 20 having a massage pillar 10 rotationally coupled to the cylindrical body 20 for vertically adjusting its height in order to adjust the magnitude and evenness of the pressure in contact with the acupunctural points on the sole of the foot.

Please refer to FIG. 2 for the structure of the prior-art sole-massaging shoes disclosed in R.O.C. Patent Publication No. 271550, comprising an insole 30 with a wooden surface made according to the geometric curvature of the sole of a human body; a meshed sole 40 disposed on the surface of the wooden insole 30; a plurality of spherical protrusions disposed on the wooden insole 30 and passing through the meshed sole 40 to provide a massage to the wearer's sole during walking.

Please refer to FIG. 3 for the massaging sole disclosed in R.O.C. Patent Publication No. 307791, comprising a sole 60, a plurality of holes on the surface for letting the massage protrusions 50 pass through, and a filling stuffed inside massage protrusion 50 for support, where the filling could be made of a magnetic or far infrared material, wherein the far infrared material is built-in and the action surface is isolated by the massage protrusions. As a result, this blocks the far infrared and theoretically provides a reduced effect.

Please refer to FIG. 4 for the massaging sole disclosed in the R.O.C. Patent Publication No. 510219, comprising a thin plate with a plurality of holes; a fixture disposed under the thin plate; and a fixed massage member passing through the holes.

As shown in the related massaging sole design of the prior art, the massage protrusions constitute a hard structure, and the binding force of the shoe has to be the same as regular shoes to allow the foot to wear the shoe with a binding force.

Further, the hard massage protrusions will produce a depression on the tissue of the sole after a long time wearing of such shoes.

Therefore, the present invention provides a floating massage protrusion. The arrangement of a plurality of the floating massage protrusions forms a soft touching pad with even pressure, similar to walking on a soft sponge surface, and gives a very soft and smooth feeling. Currently, enhancement for comparable new shoes generally uses air cushions as buffers. The air-cushioned shoes are used as jogging shoes or sport shoes, and not only provide a better bouncing effect to the human body, but also offer more comfortable wear for walking. The shoes include a binding force suited to the variation of elasticity of the pad of the air-cushion shoes. Therefore, when we lift up our leg and foot, the binding force of the shoe forms an appropriate binding force to wrap the sole by the reaction of the elasticity of the pad of the air-cushion shoes so that the sole and instep will not be bounded too tightly, but will provide a very comfortable wear instead. The present invention will accomplish the same comfortable effect when it is applied to shoes. Furthermore, since the massage protrusion is floating, the massage protrusion will be in contact with the wearer's skin surface before the massage actually takes place, and the sensation of such contact will be sent to the central nervous system. The central nervous system will inform the acupunctural points of where the massage will be given, and the wearer will be psychologically prepared to take the massage. Such psychological preparation will affect the pain of the massage. When the massage stops, it will provide a caressing effect to the skin surface at the acupunctural points, which can psychologically comfort the wearer.

Since the massage protrusion is in the floating state, the user receiving the massage will receive the massage from different angles achieved by simulating the rubbing movements.

Of course, if the present invention is applied to the cushion of a chair, it also can accomplish the aforementioned psychological massaging and caressing effects and the practical functions in the process when a sitter changes his/her sitting position.

SUMMARY OF THE PREFERRED EMBODIMENTS

The primary objective of the present invention is to provide a pad having a plurality of massage protrusions in its lining, the massage protrusions forming a structure in a floating state under normal conditions; a plurality of floating chambers being disposed within the surface of the pad for supporting the massage protrusions and limiting the range of their activity; an opposing member disposed under each of the massage protrusion; and a pair of repulsive magnetic members respectively disposed on each of the massage protrusions and its corresponding opposing member for keeping the massage protrusions in the state of floating under normal conditions by means of the repulsive magnetism, and providing the magnetic lines to the blood flowing through the related acupunctural points for magnetic treatment.

BRIEF DESCRIPTION OF THE DRAWINGS

Other features and advantages of the present invention will become apparent in the following detailed description of the preferred embodiments with reference to the accompanying drawings, in which.

DETAILED DESCRIPTION OF THE INVENTION

Figure 5:
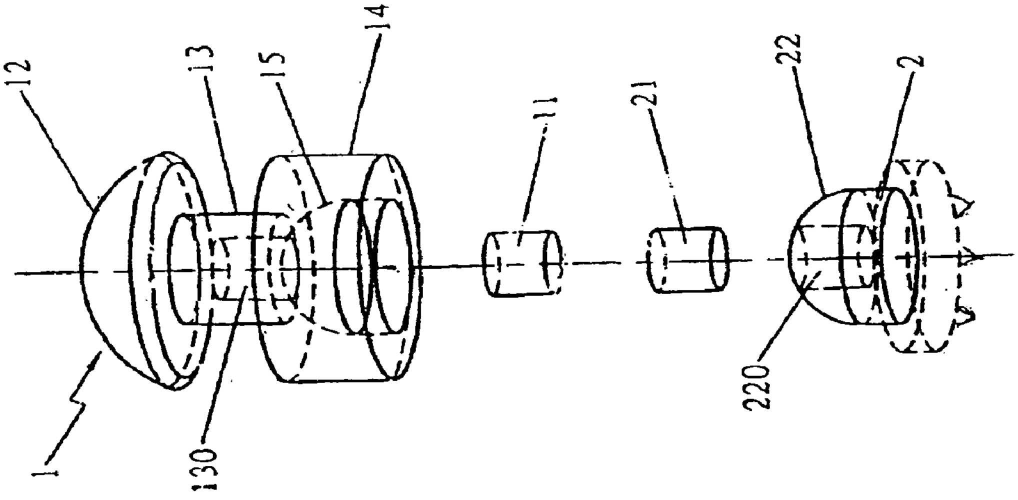
FIG. 5 is a perspective diagram of the construction of a massage protrusion and its corresponding opposing member according to the present invention.

Please refer to FIG. 5 for a detailed illustration of the present invention, which comprises a mushroom-shaped massage protrusion 1; an inner circular body 15 formed at a root section 14; an upper hemispherical body 12 connected to a neck section 13; a magnetic member 11 in the massage protrusion 1 being installed into an inner hole 130 at the neck section 13; an opposing member 2 disposed under the corresponding massage protrusion 1, and the upper end of the opposing member being an outer circular body 22, similarly having an inner hole 220 in the lining to embed a magnetic member 21.

Figure 1:
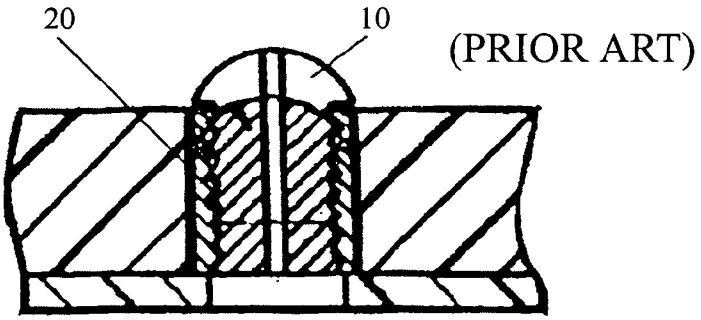
FIGS. 1 to 4 are illustrative diagrams of the structure of massage pads according to the prior art.
Figure 2:
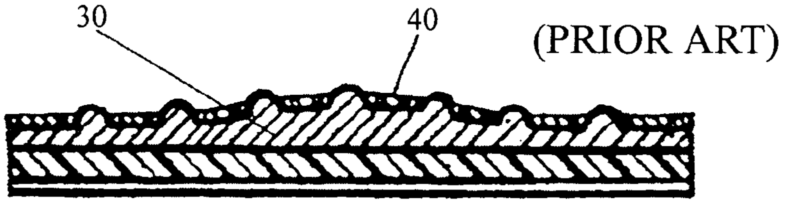
Figure 3:
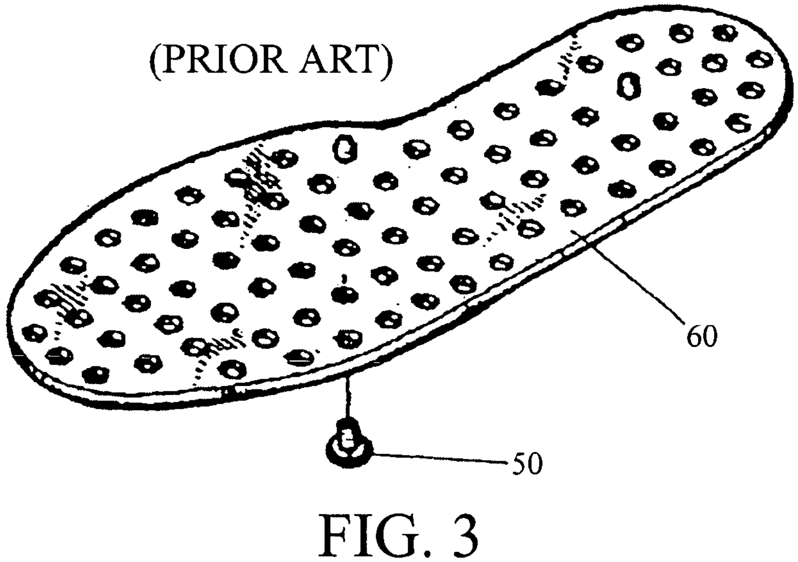
Figure 4:
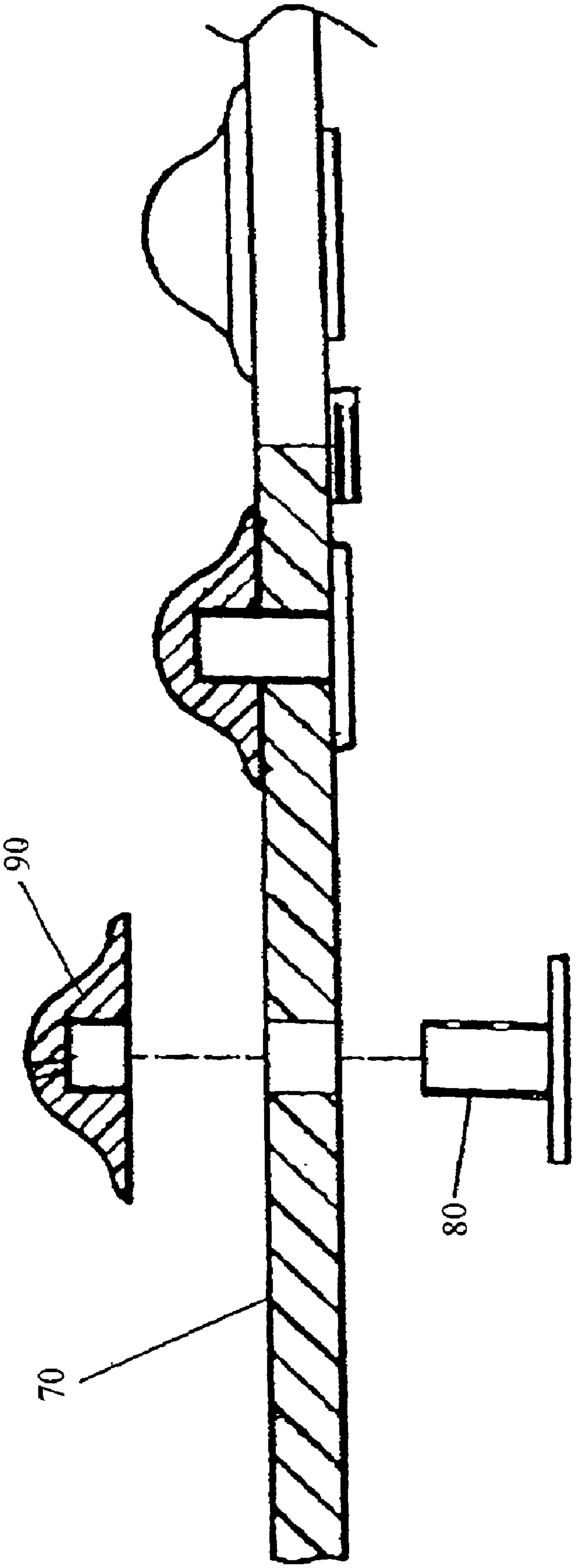
(PRIOR ART) FIG. 4
Figure 6:
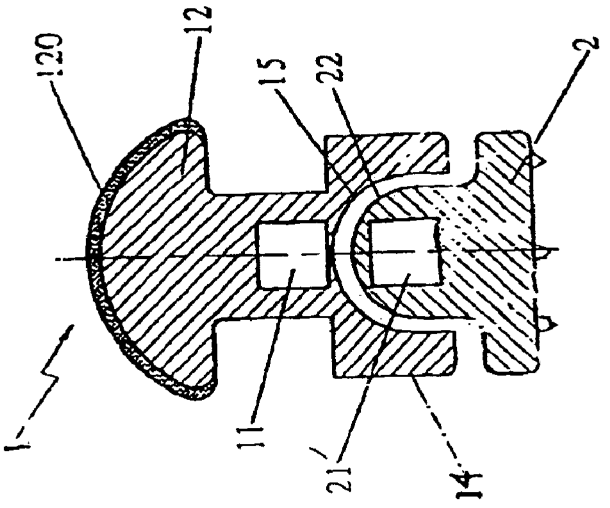
FIG. 6 is a side-view diagram of the assembly of the massage protrusion and its corresponding opposing member according to the present invention.

Please refer to FIG. 6. When the massage protrusion 1 is connected with its corresponding opposing member 2, the two magnetic members 11, 21 repel each other. The inner circular body 15 is formed at the root section with its lower end supported by the exterior of the outer circular body 22 disposed on the opposing member 2. The massage protrusion 1 and the opposing member 2 can be made of a ceramic material. In the manufacturing process, a far infrared converting material such as feldspar, magnesium oxide, or zirconium oxide can be added to achieve sintering and form an integral body. Other materials can be used so that the surface of the upper hemispherical body 12 of the massage protrusion 1 at least forms a far infrared converting layer 120. The converting layer 120 provides direct body heat absorption during the massage process, and radiates the heat in the opposite direction at the blood capillaries of the acupunctural points and to stimulate the blood. The wavelength can be synchronized to a wavelength acceptable by the human body that produces a resonance with the electrons within the cells. The energy of its vibration will be amplified to stimulate the blood. The magnetic member 11 also will form magnetic field lines that have a magnetic effect for the blood capillaries adjacent to the acupunctural points.

Figure 7:
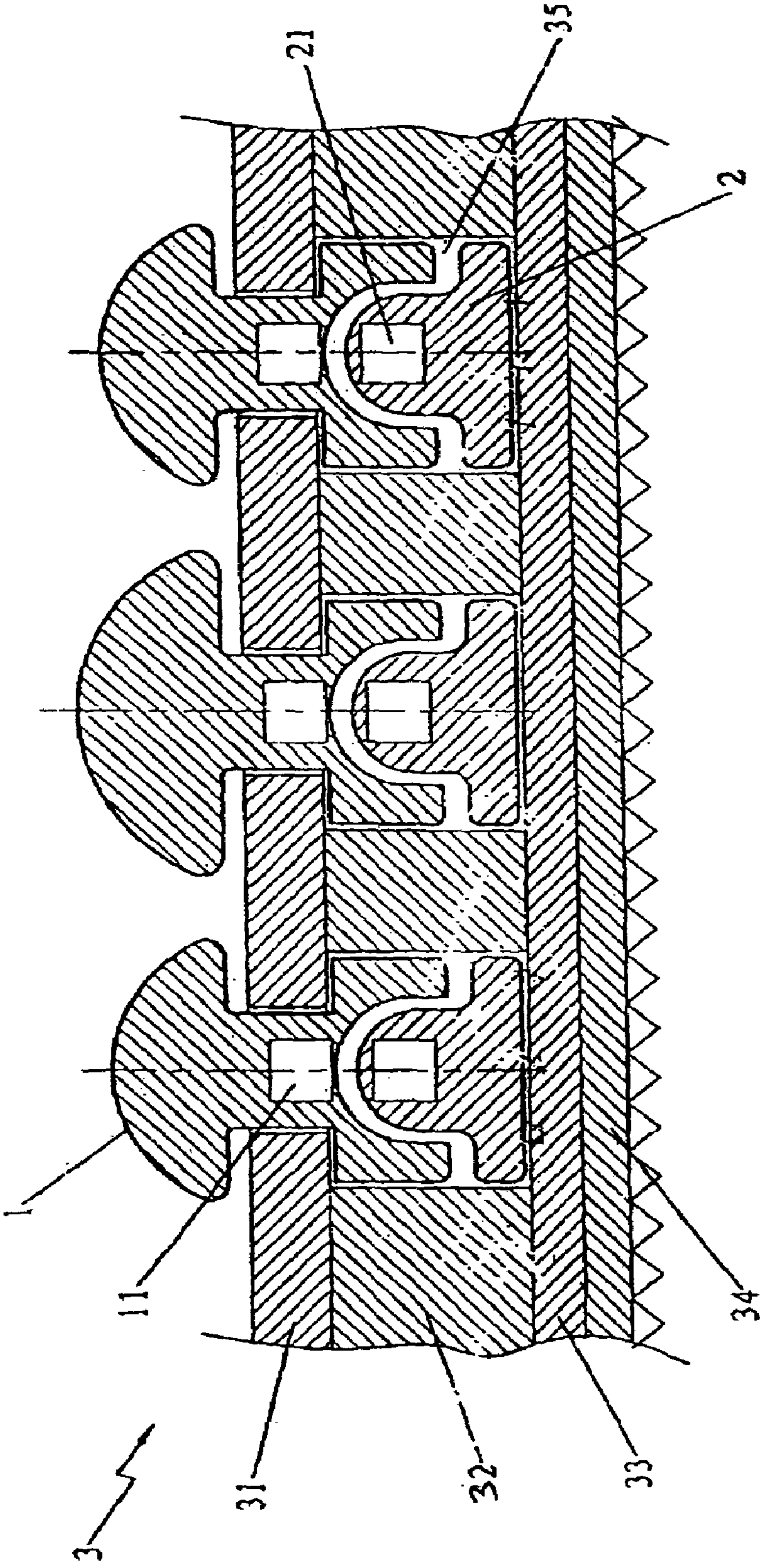
FIG. 7 is a cross-section diagram of an assembled pad according to a preferred embodiment of the present invention.

Please refer to FIG. 7. When the assembled massage protrusion 1 is placed into a floating chamber 35 of the pad 3, wherein the pad 3 comprises a mat 31, a middle lining 32, and a pad plate 33; preferably, a slip-resistant layer 34 is added at the bottom of the pad 3. The pad plate 33 can be made of a harder material, while the mat 31 and the middle lining 32 can be made of a softer material to provide elastic deformation, so that the restoration of such elastic deformation can produce the effect of raising the massage protrusion 1.

When the floating massage pad of the present invention is not stepped on, the repulsion between the mutually repelling magnetic members 11, 21, respectively disposed on the massage protrusion 1 and its corresponding opposing member 2, keeps the massage protrusion in a floating state. Further, the massage protrusion is restricted by the floating chamber 35 to prevent it from being separated from the pad.

Figure 8:
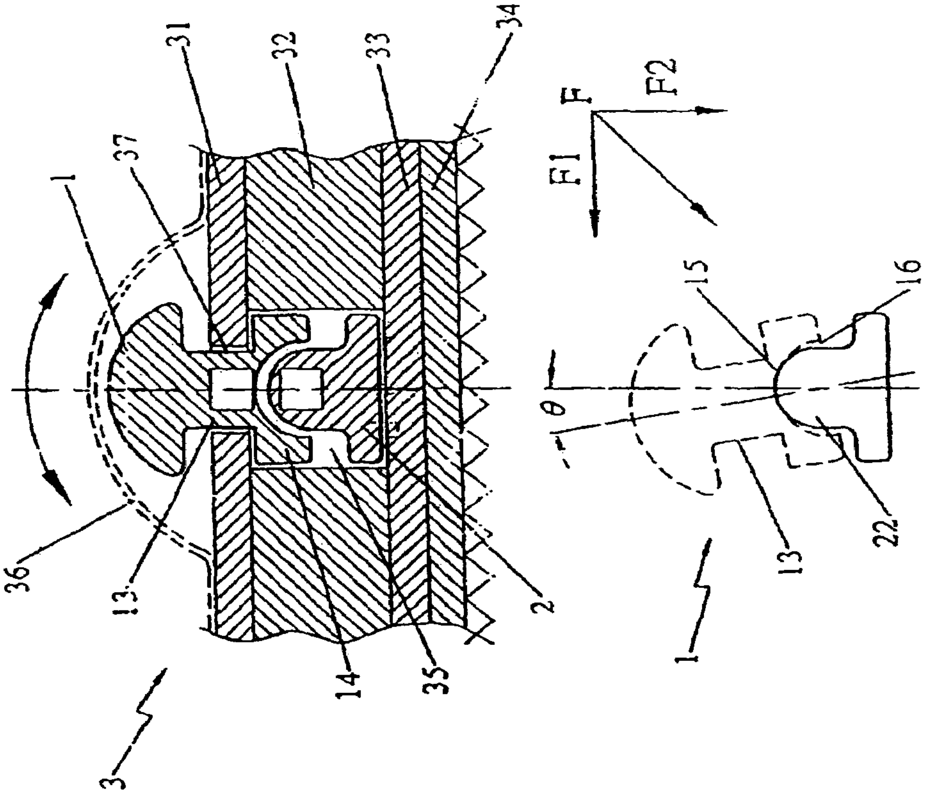
FIG. 8 is an illustrative diagram of the action of the massage protrusion with respect to the pad according to the present invention.

Please refer to FIG. 8. The massage protrusion 1 is movably coupled to a through hole 37 on the pad 3 by the neck section 13, and is connected to an inner circular body 15 disposed at the root section 14 of the bottom of the massage protrusion 1, so that the massage protrusion 1 will not fall out, but can move vertically in the floating chamber 35. When the massage protrusion 1 receives pressure and presses down onto the isolated opposing member 2, which is disposed under the massage protrusion 1 and is supported on the pad plate 33, the pressure will be transmitted to the pad plate 33. The slip-resistant layer 34 can be made of an elastic material to increase the elastic effect, which will provide a softer feel when the user walks on the pad and also makes it easier to bend the pad. As shown in the lower section of the figure, the massage protrusion 1 is moved to a deflection angle θ due to an external force F, and the center of the deflection angle θ resides at the intersection of its axis at the top of the outer circular body 22. The pivoting connection is formed by the movement of the inner circular body 15 provided in the massage protrusion 1 and the related cylindrical surface of the outer circular body 22, and which is in contact with an opening 16 to provide a limiting point to limit the movement.

Further, during any movement, pressure from the neck section 13 is exerted on the surface of the inner circular surface of the through hole 37 in the mat 31, such that the through hole 37 deforms. When such force is exerted in an aslant direction, the action will push the massage protrusion to produce a movement, with the horizontal component force F1 acting to push for the horizontal movement and the vertical component force F2 acting to move the massage protrusion on the opposing member 2. After the massage protrusion recovers from the deformation movement produced by the action F, it is erected in an upright position.

Figure 9:
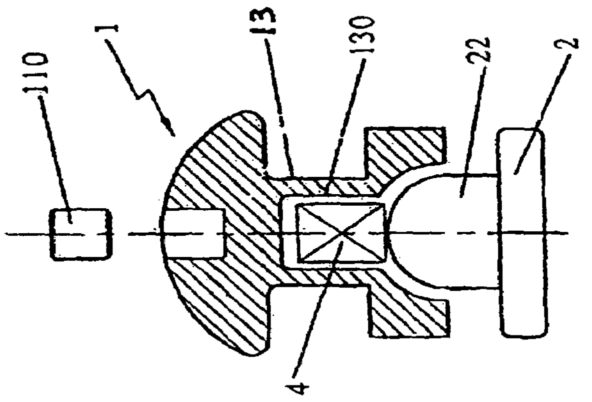
FIG. 9 is an illustrative diagram of the floating state related to the massage protrusion and its corresponding opposing member according to another preferred embodiment of the present invention.

Please refer to FIG. 9. As an alternative to the repulsion generated by the magnetic members between the massage protrusion 1 and the opposing member 2, an elastic tension component 4 disposed in the inner hole 130 of the neck section 13 and on the upper end of the outer circular body 22 of the corresponding opposing member 2 can also keep the massage protrusion in the floating state. Further, a magnetic member 110 having the effect of physical treatment can be installed at the upper hemisphere of the massage protrusion 1.

Figure 10:
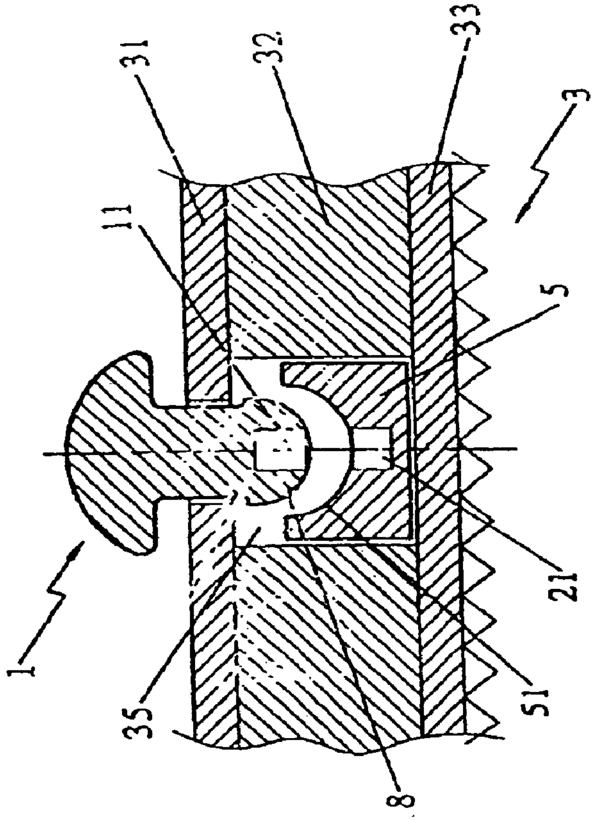
FIG. 10 is a cross-sectional diagram of the massage protrusion and a joint member according to the present invention.

Please refer to FIG. 10 for another embodiment the present invention. To further facilitate the assembling and assure the mechanical strength of the massage protrusion, a joint 5 can be installed in an opposite direction in the floating chamber 35 of the pad 3. The joint 5 also has an inner circular body 51 and a magnetic member 21 to provide the joint connection with the corresponding outer circular body 18. A magnetic member 11 is also disposed in the corresponding outer circular body 18 of the massage protrusion 1, such that the massage protrusion 1 is kept in the floating state by the magnetic repulsion.

Figure 11:
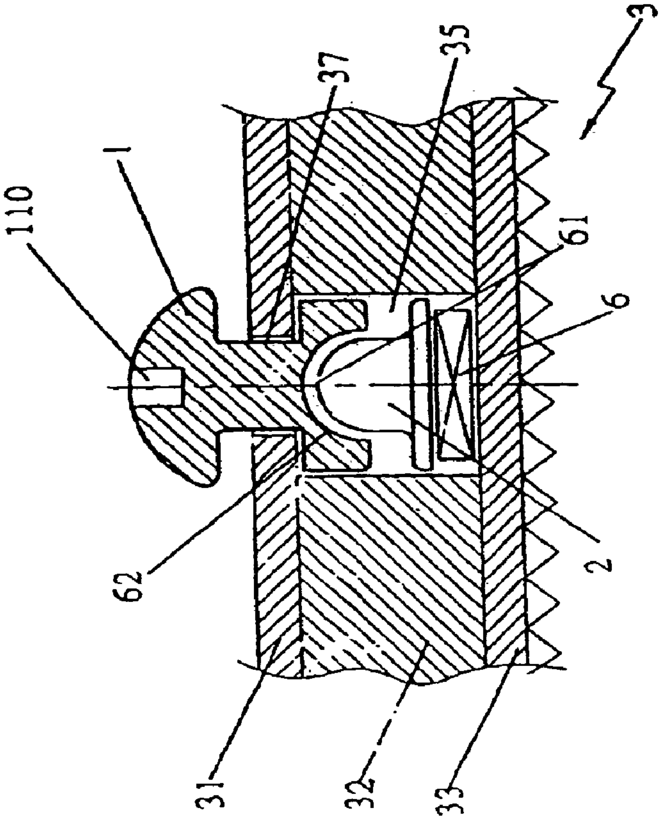
FIG. 11 is a cross-sectional diagram of an elbow joint of the massage protrusion according to the present invention.

Please refer to FIG. 11 for the present invention, where the whole massage protrusion 1 is kept in the floating state. By means of an elastic pad, a magnetic member 110 with the effect of physical treatment can be installed at the upper section of the massage protrusion 1, and a joint socket 62 is disposed at the lower section, such that the joint socket 62 is movably disposed in the joint head 61 of the opposing member 2. An elastic pad 6 is installed at the bottom of the opposing member 2 and integrally installed in the floating chamber 35, and the range of activity for the massage protrusion 1 is also limited by the through hole 37 on the pad 3.

Figure 12:
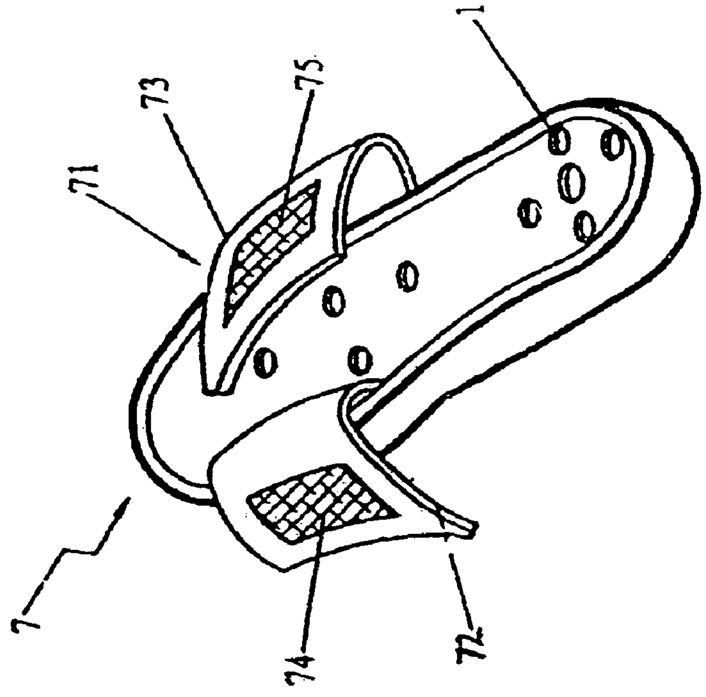
FIG. 12 is an illustrative diagram of the floating massage pad being applied to shoes according to the present invention.

Please refer to FIG. 12 for the present invention being applied to a shoe 7. If the present invention is applied on the sole, then its surface has a set of massage protrusions 1 corresponding to the acupunctural points of the human body. The size of the massage protrusions can be varied according to the area of the acupunctural point. A vamp 71 is placed in front of the shoe body 7, and the vamp 71 includes an inner vamp 73 and an outer vamp 72 mutually connected by a buckle 74, 75 to adjust the size of the vamp to wrap around the sole of the foot.

Figure 13:
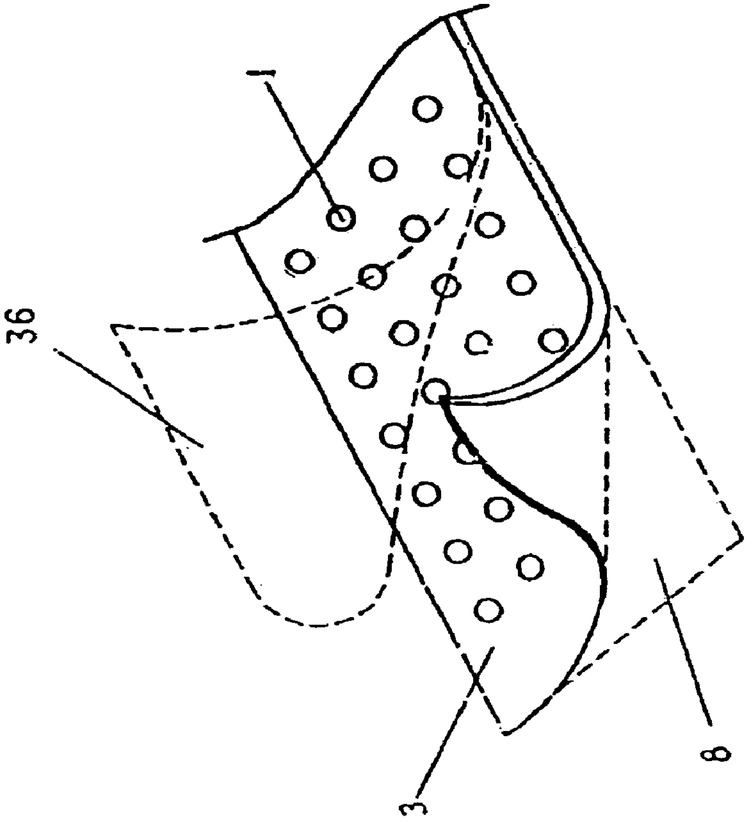
FIG. 13 is an illustrative diagram of additional decoration on the surface of a preferred embodiment of the present invention.

Please refer to FIG. 13 for the present invention. After the massage protrusion 1 is assembled onto the upper surface of the pad 3, an isolating layer 36 is used to isolate and prevent water vapor and dust, or even provide a disinfecting effect. The implementation of such isolating layer requires an appropriately reserved space for the range of movement of the massage protrusion 1 in order to provide the space for the movement of the massage protrusion 1.

Figure 14:
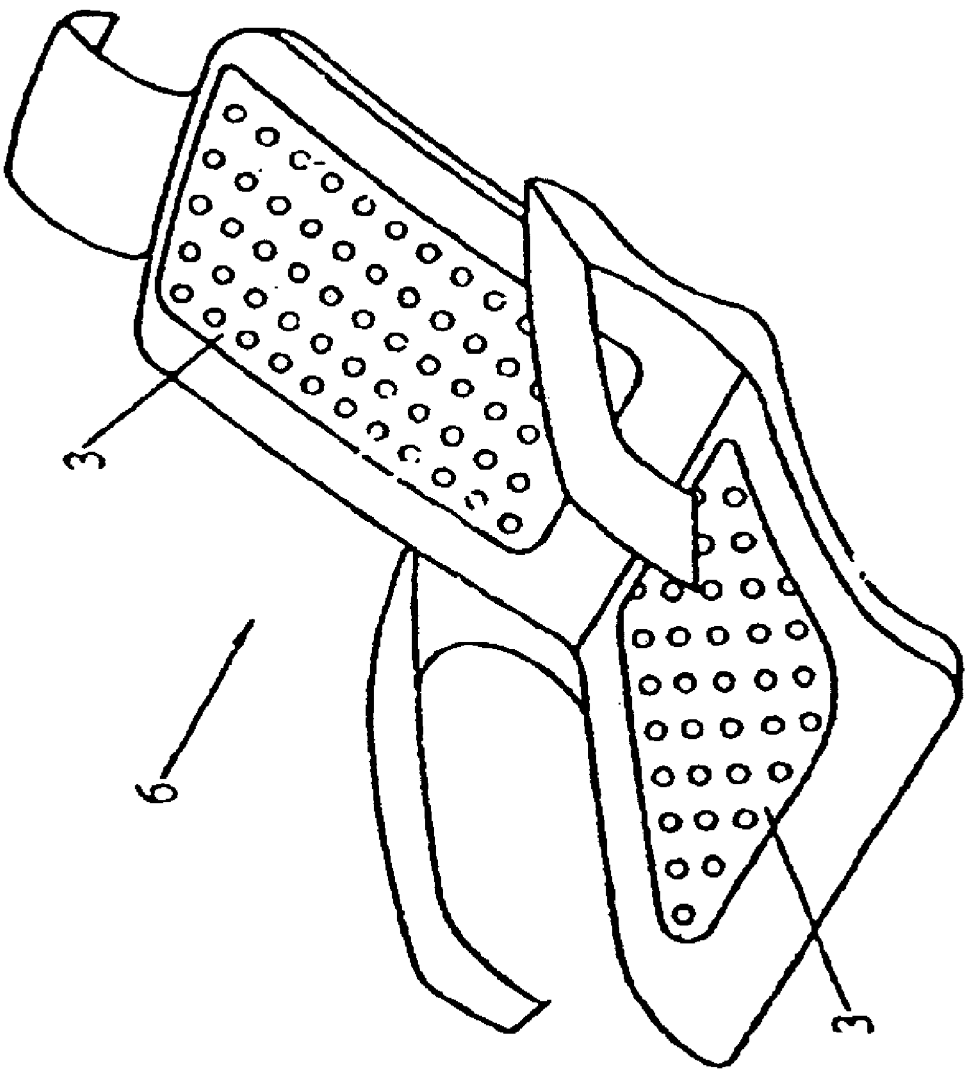
FIG. 14 is an illustrative diagram of the floating massage pad being applied to chairs according to the present invention.

Further, an attachment interface 8 of a buckle can be installed under the pad 3. The attachment interface 8 can be applied to the cushion or the surface of the back of a chair 6 as shown in FIG. 14 to attach the pad 3 onto the surface of the cushion or the back of the chair 6. Such attachment interface 8 can be attached by means of an adhesive layer or a gluing layer.

What is claimed is:

1. A floating massage pad structure, comprising:

a pad having an opening disposed on a top surface of the pad;

a chamber disposed in the pad and located under the opening;

a massage protrusions comprising:

an upper hemispherical body movably disposed on the top surface;

a root section disposed in the chamber and coupled to the upper hemispherical body through the opening;

an opposing member disposed in the chamber under the root section of massage protrusion;

a pair of magnetic members, one disposed in the massage protrusion and another disposed in the opposing member, wherein the pair of magnetic members are configured to repel the massage protrusion and the opposing member and wherein the massage protrusion further includes a concave opening in the root section and the opposing member includes a convex portion matched to the concave opening.

2. The floating massage pad structure of claim 1, wherein the pad comprises a middle sole attached by an upper mat and a lower mat, and preferably with a pad plate.

3. The floating massage pad structure of claim 1, wherein the pad at its bottom has an elastic slip-resistant layer.

4. The floating massage pad structure of claim 1, wherein the massage protrusion further comprises an inner hole at the upper section of the opposing member for installing an elastic tension component.

5. The floating massage pad structure of claim 1, wherein the massage protrusion in its lower section has an outer circular body acting on a joint disposed in the inner circular body, and a pair of repulsive magnetic members respectively disposed on the inner circular body and the outer circular body.

6. The floating massage pad structure of claim 1, wherein the massage protrusion is made of a ceramic material.

7. The floating massage pad structure of claim 1, wherein the upper hemispherical body includes a far infrared converting layer on a top surface.

8. The floating massage pad structure of claim 1 further comprising an adhesive interface on a lower layer.

9. The floating massage pad structure of claim 1 further comprising an isolating layer covering the massage protrusion, the isolating layer including space for the movement of upper hemispherical body.

* * * * *